(12) United States Patent
Yung et al.

(10) Patent No.: US 7,354,582 B2
(45) Date of Patent: Apr. 8, 2008

(54) USE OF VEGF ANTAGONISTS FOR THE TREATMENT OF MALIGNANT GLIOMAS

(75) Inventors: W. K. Alfred Yung, Houston, TX (US); Candelaria Gomez-Manzano, Houston, TX (US); Juan Fueyo, Houston, TX (US); Jesse M. Cedarbaum, Larchmont, NY (US); Jocelyn Holash, Alameda, CA (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 44 days.

(21) Appl. No.: 11/373,462

(22) Filed: Mar. 10, 2006

(65) Prior Publication Data

US 2007/0212354 A1 Sep. 13, 2007

(51) Int. Cl.
*A61K 38/18* (2006.01)
*C07K 14/71* (2006.01)
*C12N 15/62* (2006.01)

(52) U.S. Cl. .............................. 424/134.1; 424/192.1; 514/2; 514/12; 530/350; 536/23.4

(58) Field of Classification Search ..................... None
See application file for complete search history.

(56) References Cited

U.S. PATENT DOCUMENTS 6,897,294 B2 * 5/2005 Davis-Smyth et al. ...... 530/350

OTHER PUBLICATIONS

Gerber, H., et al., (2000) Cancer Res., 60:6253-6258.
Kim, E., et al., (2002) PNAS, 99(17):11399-11404.
Holash, J., et al., (2002) PNAS, 99(17):11393-11398.

* cited by examiner

*Primary Examiner*—Christine J Saoud
*Assistant Examiner*—Jon M Lockard
(74) *Attorney, Agent, or Firm*—Valeta Gregg, Esq.

(57) ABSTRACT

Methods for treating a human patient suffering from a brain tumor, including glioblastoma, by administering an effective amount of a vascular endothelial growth factor (VEGF) inhibitor to the human patient. The VEGF inhibitor is a VEGF antagonist protein comprising a dimeric protein having two fusion polypeptides having the sequence of SEQ ID NO:2.

12 Claims, No Drawings

SEQUENCE LISTING

<160> NUMBER OF SEQ ID NOS: 2

<210> SEQ ID NO 1
<211> LENGTH: 1377
<212> TYPE: DNA
<213> ORGANISM: homo sapiens

<400> SEQUENCE: 1

```
atggtcagct actgggacac cggggtcctg ctgtgcgcgc tgctcagctg tctgcttctc      60
acaggatcta gttccggaag tgataccggt agacctttcg tagagatgta cagtgaaatc     120
cccgaaatta tacacatgac tgaaggaagg gagctcgtca ttccctgccg ggttacgtca     180
cctaacatca ctgttacttt aaaaaagttt ccacttgaca ctttgatccc tgatggaaaa     240
cgcataatct gggacagtag aaagggcttc atcatatcaa atgcaacgta caaagaaata     300
gggcttctga cctgtgaagc aacagtcaat gggcatttgt ataagacaaa ctatctcaca     360
catcgacaaa ccaatacaat catagatgtg gttctgagtc cgtctcatgg aattgaacta     420
tctgttggag aaaagcttgt cttaaattgt acagcaagaa ctgaactaaa tgtggggatt     480
```

```
gacttcaact gggaataccc ttcttcgaag catcagcata agaaacttgt aaaccgagac     540
ctaaaaaccc agtctgggag tgagatgaag aaatttttga gcaccttaac tatagatggt     600
gtaacccgga gtgaccaagg attgtacacc tgtgcagcat ccagtgggct gatgaccaag     660
aagaacagca catttgtcag ggtccatgaa aaggacaaaa ctcacacatg cccaccgtgc     720
ccagcacctg aactcctggg gggaccgtca gtcttcctct ccccccaaa acccaaggac     780 accctcatga tctcccggac ccctgaggtc acatgcgtgg tggtggacgt gagccacgaa     840
gaccctgagg tcaagttcaa ctggtacgtg gacggcgtgg aggtgcataa tgccaagaca     900
aagccgcggg aggagcagta caacagcacg taccgtgtgg tcagcgtcct caccgtcctg     960
caccaggact ggctgaatgg caaggagtac aagtgcaagg tctccaacaa agccctccca    1020
gcccccatcg agaaaaccat ctccaaagcc aaagggcagc ccgagaacc acaggtgtac    1080 accctgcccc catcccggga tgagctgacc aagaaccagg tcagcctgac ctgcctggtc    1140
aaaggcttct atcccagcga catcgccgtg gagtgggaga gcaatgggca gccggagaac    1200
aactacaaga ccacgcctcc cgtgctggac tccgacggct ccttcttcct ctacagcaag    1260
ctcaccgtgg acaagagcag gtggcagcag gggaacgtct tctcatgctc cgtgatgcat    1320
gaggctctgc acaaccacta cacgcagaag agcctctccc tgtctccggg taaatga      1377
```

<210> SEQ ID NO 2  
<211> LENGTH: 458  
<212> TYPE: PRT  
<213> ORGANISM: homo sapiens

<400> SEQUENCE: 2

```
Met Val Ser Tyr Trp Asp Thr Gly Val Leu Leu Cys Ala Leu Leu Ser
 1               5                  10                  15

Cys Leu Leu Leu Thr Gly Ser Ser Ser Gly Ser Asp Thr Gly Arg Pro
            20                  25                  30

Phe Val Glu Met Tyr Ser Glu Ile Pro Glu Ile Ile His Met Thr Glu
        35                  40                  45

Gly Arg Glu Leu Val Ile Pro Cys Arg Val Thr Ser Pro Asn Ile Thr
    50                  55                  60

Val Thr Leu Lys Lys Phe Pro Leu Asp Thr Leu Ile Pro Asp Gly Lys
65                  70                  75                  80

Arg Ile Ile Trp Asp Ser Arg Lys Gly Phe Ile Ile Ser Asn Ala Thr
                85                  90                  95

Tyr Lys Glu Ile Gly Leu Leu Thr Cys Glu Ala Thr Val Asn Gly His
            100                 105                 110

Leu Tyr Lys Thr Asn Tyr Leu Thr His Arg Gln Thr Asn Thr Ile Ile
        115                 120                 125

Asp Val Val Leu Ser Pro Ser His Gly Ile Glu Leu Ser Val Gly Glu
    130                 135                 140

Lys Leu Val Leu Asn Cys Thr Ala Arg Thr Glu Leu Asn Val Gly Ile
145                 150                 155                 160

Asp Phe Asn Trp Glu Tyr Pro Ser Ser Lys His Gln His Lys Lys Leu
                165                 170                 175

Val Asn Arg Asp Leu Lys Thr Gln Ser Gly Ser Glu Met Lys Lys Phe
            180                 185                 190

Leu Ser Thr Leu Thr Ile Asp Gly Val Thr Arg Ser Asp Gln Gly Leu
        195                 200                 205

Tyr Thr Cys Ala Ala Ser Ser Gly Leu Met Thr Lys Lys Asn Ser Thr
```

-continued

```
              210                 215                 220
Phe Val Arg Val His Glu Lys Asp Lys Thr His Thr Cys Pro Pro Cys
225                 230                 235                 240

Pro Ala Pro Glu Leu Leu Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
            275                 280                 285

Tyr Val Asp Gly Val Glu Val His Asn Ala Lys Thr Lys Pro Arg Glu
        290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Ala Pro Ile Glu Lys Thr Ile Ser Lys Ala Lys Gly
                340                 345                 350

Gln Pro Arg Glu Pro Gln Val Tyr Thr Leu Pro Pro Ser Arg Asp Glu
            355                 360                 365

Leu Thr Lys Asn Gln Val Ser Leu Thr Cys Leu Val Lys Gly Phe Tyr
    370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Tyr Ser Lys Leu Thr Val Asp Lys Ser Arg Trp Gln Gln Gly Asn
            420                 425                 430

Val Phe Ser Cys Ser Val Met His Glu Ala Leu His Asn His Tyr Thr
            435                 440                 445

Gln Lys Ser Leu Ser Leu Ser Pro Gly Lys
450                 455
```

USE OF VEGF ANTAGONISTS FOR THE TREATMENT OF MALIGNANT GLIOMAS

BACKGROUND

1. Field of the Invention

The invention relates to methods of treating patients with primary brain tumor, such as glioblastoma, by administering a vascular endothelial growth factor (VEGF) antagonist.

2. Description of Related Art

Vascular endothelial growth factor (VEGF) expression is nearly ubiquitous in human cancer, consistent with its role as a key mediator of tumor neoangiogenesis. Blockade of VEGF function, by binding to the molecule or its VEGFR-2 receptor, inhibits growth of implanted tumor cells in multiple different xenograft models (see, for example, Gerber et al. (2000) Cancer Res. 60:6253-6258). A soluble VEGF antagonist, termed a "VEGF trap" or "VEGF$_{R1R2}$ trap" has been described (Kim et al. (2002) Proc. Natl. Acad. Sci. USA 99:11399-404; Holash et al. (2002) Proc. Natl. Acad. Sci. USA 99:11393-8), which publications are herein specifically incorporated by reference in their entirety.

BRIEF SUMMARY OF THE INVENTION

In a first aspect, the invention features a method of treating a human patient suffering from a primary brain tumor, comprising administering a therapeutically effective amount of a vascular endothelial growth factor (VEGF) antagonist to the human patient. VEGF protein antagonists are described in WO 00/75319, herein specifically incorporated by reference. In a more specific embodiment, the primary brain tumor is a grade 3 or grade 4 astrocytoma. In a more specific embodiment, the grade 4 astrocytoma is glioblastoma.

According to the present invention, the VEGF antagonist is a fusion protein comprising immunoglobulin (Ig)-like domain components from two different VEGF receptor proteins fused to a multimerizing component. More specifically, the VEGF protein antagonists of the invention comprise a dimer of two fusion polypeptides, each polypeptide comprising an immunoglobulin (Ig)-like domain 2 of a Flt-1 and an Ig-like domain 3 of Flk-1 (also termed KDR) or Flt-4 and a multimerizing component. The VEGF antagonists used in the method of the invention encompass preferred soluble fusion polypeptides selected from the group consisting of acetylated Flt-1(1-3)-Fc, Flt-1(1-3$_{R->N}$)-Fc, Flt-1 (1-3$_{AB}$)-Fc, Flt-1(2-3$_{AB}$)-Fc, Flt-1(2-3)-Fc, Flt-1D2-VEGFR3D3-FcΔC1(a), Flt-1D2-Flk-1D3-FcΔC1(a), and VEGFR1R2-FcΔC1(a). In a specific and preferred embodiment, the VEGF antagonist is VEGFR1R2-FcΔC1(a) (also termed VEGF trap$_{R1R2}$) having the nucleotide sequence set forth in SEQ ID NO: 1 and the amino acid sequence set forth in SEQ ID NO: 2. The invention encompasses the use of a VEGF antagonist that is at least 90%, 95%, 98%, or at least 99% homologous with the nucleotide sequence set forth in SEQ ID NO: 1 and/or the amino acid sequence set forth in SEQ ID NO:2.

Administration of the VEGF antagonist may be by any method known in the art, including intraventricular, intraparenchymal, intracavitary, or convection-enhanced delivery into the brain or the tumor bed, or systemically via subcutaneous, intramuscular, intradermal, intraperitoneal, or intravenous administration. In a preferred embodiment, the VEGF antagonist is administered by subcutaneous injection or intravenous injection.

In a second aspect, the invention features a method of treating a human patient diagnosed with glioblastoma, comprising administering a therapeutically effective amount of a vascular endothelial growth factor (VEGF) antagonist to the human patient. In a preferred embodiment, the VEGF antagonist administered is a dimer comprised of two fusion polypeptides having the sequence of SEQ ID NO:2.

In a further embodiment of the method of the invention, the VEGF antagonist is combined with a second chemotherapeutic agent. Examples of chemotherapeutic agents which can be used in the method of the invention are described below, and include temozolomide (TEMODAR®; Schering Plough), irinotecan (CAMPTOSAR®; Rhone Puolenc Rorer), carboplatin (PARAPLATIN®; Bristol-Myers Squibb), oxaliplatin (ELOXATIN®; Sanofi-Aventis), nitrosoureas, lomustine (CeeNU®; Bristol-Myers Squibb), vincristine (ONCOVIN®; Gensia Sicor), vinblastine (VALBAN®; Gensia Sicor), procarbazine (MATULANE®; Sigma-tau), EGF receptor blockers such as cetuximab (ERBITUX®; Imclone Systems), pertuzumab (OMNITARG™, Genentech), erlotinib (TARCEVA®, OSI), gefitinib (IRESSA®, AstraZeneca) and imatinib mesylate (GLEEVEC®, Novartis), multi-targeted tyrosine kinase inhibitors such as sorafenib (NEXAVAR®, Bayer) or sunitinib malate (SUTENT®, Pfizer). Additional therapeutics useful in the method of the invention include sirolimus (RAPAMUNE®; Wyeth), RAD001 (Novartis), Sutan, Divalproes (DEPAKOTE®; Abbott), and p13K and AKT inhibitors. The second therapeutic agent may be administered.

Other objects and advantages will become apparent from a review of the ensuing detailed description.

DETAILED DESCRIPTION

Before the present methods are described, it is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present invention will be limited only the appended claims. All applications mentioned herein are specifically incorporated by reference in their entirety.

As used in this specification and the appended claims, the singular forms "a", "an", and "the" include plural references unless the context clearly dictates otherwise. Thus for example, a reference to "a method" includes one or more methods, and/or steps of the type described herein and/or which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described.

General Description

Glioblastoma is the most common intrinsic brain tumor in adults and is one of the most aggressive human neoplasms. The median survival for a patient with newly diagnosed glioblastoma is about 1 year, despite maximum surgical and medical intervention. Less than 5% of patients are alive 3 years following diagnosis (Nigro et al. (2005) Cancer Res 65:1678). It is recognized that new strategies for the treatment of glioblastoma are needed. Among targets suitable for new therapies are regulators of angiogenesis. These molecules are especially important in gliomas because hypervascularization is a major feature of these tumors. The progression of an astrocytoma from a low-grade to high-grade malignancy is characterized by increased neovascularization (Im et al. (1999) Cancer Res 59:895-900). Several lines of evidence suggest that overexpression of VEGF and its receptors are responsible for angiogenesis in human malignant gliomas.

Vascular endothelial growth factor/vascular permeability factor (VEGF) was initially identified as a tumor-derived factor capable of increasing vascular permeability. It was subsequently found to be a proliferative factor for endothelial cells. In the embryo, VEGF is absolutely essential for the development of the vasculature. In the adult, VEGF is up-regulated in a variety of normal and pathological processes associated with increased vascular permeability and angiogenesis.

The family of VEGF-related angiogenic growth factors is comprised of VEGF itself (VEGF-A) and the related proteins VEGF-B, -C, -D and E, and placental growth factor (PLGF). In addition, there are at least four different isoforms of VEGF-A. However, as some members of the family have only recently been identified, their biological importance is still poorly understood. The actions of VEGF and its related factors are mediated by a group of three receptor tyrosine kinases, VEGFR1, VEGFR2 and VEGFR3.

Consistent with predictions from animal studies, blockade of VEGF using a humanized monoclonal antibody has emerged reporting promising results in cancer patients, based on preliminary reports from early clinical trials (Bergsland et al. (2000) ASCO Abstract #939). The VEGF antagonist protein, because of its greater affinity for VEGF and its ability to bind other VEGF family members such as the PlGFs, is a potent and useful anti-cancer therapeutic agent.

Definitions

By the term "therapeutically effective dose" is meant a dose that produces the desired effect for which it is administered. The exact dose will depend on the purpose of the treatment, and will be ascertainable by one skilled in the art using known techniques (see, for example, Lloyd (1999) The Art, Science and Technology of Pharmaceutical Compounding). Efficacy can be measured in conventional ways, depending on the condition to be treated. For cancer therapy, efficacy can, for example, be measured by assessing the time to disease progression, or determining the response rates. Therapeutically effective amount also refers to a target serum concentration, such as a trough serum concentration, that has been shown to be effective in suppressing disease symptoms when maintained for a period of time.

By the term "blocker", "inhibitor", or "antagonist" is meant a substance that retards or prevents a chemical or physiological reaction or response. Common blockers or inhibitors include but are not limited to antisense molecules, antibodies, antagonists and their derivatives. More specifically, an example of a VEGF blocker or inhibitor is a VEGF receptor-based antagonist including, for example, an anti-VEGF antibody, or a VEGF antagonist such as $VEGF_{R1R2}$-FcΔC1(a) (SEQ ID NOs:1-2). For a complete description of VEGF-receptor based antagonists including $VEGF_{R1R2}$-FcΔC1(a), see PCT publication WO 00/75319.

The term "package insert" is used to refer to instructions customarily included in commercial packages of therapeutic products, that contain information about the indications, usage, dosage, administration, contraindications and/or warnings concerning the use of such therapeutic products.

The term "intravenous infusion" refers to introduction of a drug into the vein of an animal or human patient over a period of time greater than approximately 5 minutes, preferably between approximately 30 to 90 minutes, although, according to the invention, intravenous infusion is alternatively administered for 10 hours or less.

The term "subcutaneous administration" refers to introduction of a drug under the skin of an animal or human patient, preferable within a pocket between the skin and underlying tissue, by relatively slow, sustained delivery from a drug receptacle. The pocket may be created by pinching or drawing the skin up and away from underlying tissue.

The VEGF Trap Antagonist

In a preferred embodiment, the VEGF antagonist is a receptor-Fc fusion protein consisting of the principal ligand-binding portions of the human VEGFR1 and VEGFR2 receptor extracellular domains fused to the Fc portion of human IgG1. Specifically, the VEGF antagonist consists of Ig domain 2 from VEGFR1, which is fused to Ig domain 3 from VEGFR2, which in turn is fused to the Fc domain of IgG1 (SEQ ID NO:2).

In a preferred embodiment, an expression plasmid encoding the VEGF antagonist is transfected into CHO cells, which secrete VEGF antagonist into the culture medium. The resulting VEGF antagonist is a dimeric glycoprotein with a protein molecular weight of 97 kDa and contains ~15% glycosylation to give a total molecular weight of 115 kDa.

Since the VEGF antagonist binds its ligands using the binding domains of high-affinity receptors, it has a greater affinity for VEGF than do monoclonal antibodies. The VEGF antagonist binds VEGF-A ($K_D$=0.5 pM), PLGF1 ($K_D$=1.3 nM), and PLGF2 ($K_D$=50 pM); binding to other VEGF family members has not yet been fully characterized.

Combination Therapies

In numerous embodiments, a VEGF antagonist may be administered in combination with one or more additional compounds or therapies, including a second VEGF antagonist, a chemotherapeutic agent, surgery and/or radiation. Combination therapy includes administration of a single pharmaceutical dosage formulation which contains a VEGF antagonist and one or more additional agents; as well as administration of a VEGF antagonist and one or more additional agent(s) in its own separate pharmaceutical dosage formulation. For example, a VEGF antagonist and a cytotoxic agent, a chemotherapeutic agent or a growth inhibitory agent can be administered to the patient together in a single dosage composition such as a combined formulation, or each agent can be administered in a separate dosage formulation. Where separate dosage formulations are used, the VEGF-specific fusion protein of the invention and one or more additional agents can be administered concurrently, or at separately staggered times, i.e., sequentially.

The term "cytotoxic agent" as used herein refers to a substance that inhibits or prevents the function of cells and/or causes destruction of cells. The term is intended to include radioactive isotopes (e.g. $I^{131}$, $I^{125}$, $Y^{90}$ and $Re^{186}$), chemotherapeutic agents, and toxins such as enzymatically active toxins of bacterial, fungal, plant or animal origin, or fragments thereof.

A "chemotherapeutic agent" is a chemical compound useful in the treatment of cancer. Examples of chemotherapeutic agents include alkylating agents such as thiotepa and cyclosphosphamide (Cytoxan®); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfornithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g. paclitaxel (TAXOL®, Bristol-Myers Squibb) and docetaxel (TAXOTERE®; sanofi-aventis); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylornithine (DMFO); retinoic acid; esperamicins; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY 117018, onapristone, and toremifene; and anti-androgens such as flutamide, nilutamide, bicalutamide, leuprolide, and goserelin; and pharmaceutically acceptable salts, acids or derivatives of any of the above.

A "growth inhibitory agent" when used herein refers to a compound or composition which inhibits growth of a cell, especially a cancer cell either in vitro or in vivo. Examples of growth inhibitory agents include agents that block cell cycle progression (at a place other than S phase), such as agents that induce G1 arrest and M-phase arrest. Classical M-phase blockers include the vincas (vincristine and vinblastine) and topo II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C.

Pharmaceutical Compositions

Pharmaceutical compositions useful in the practice of the method of the invention include a therapeutically effective amount of an active agent, and a pharmaceutically acceptable carrier. The term "pharmaceutically acceptable" means approved by a regulatory agency of the Federal or a state government or listed in the U.S. Pharmacopeia or other generally recognized pharmacopeia for use in animals, and more particularly, in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin.

In a preferred embodiment, the composition is formulated in accordance with routine procedures as a pharmaceutical composition adapted for intravenous, subcutaneous, or intramuscular administration to human beings. Where necessary, the composition may also include a solubilizing agent and a local anesthetic such as lidocaine to ease pain at the site of the injection. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The active agents of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The amount of the active agent of the invention that will be effective in the treatment of brain tumor can be determined by standard clinical techniques based on the present description. In addition, in vitro assays may optionally be employed to help identify optimal dosage ranges. The precise dose to be employed in the formulation will also depend on the route of administration, and the seriousness of the condition, and should be decided according to the judgment of the practitioner and each subject's circumstances. Effective doses may be extrapolated from dose-response curves derived from in vitro or animal model test systems.

For systemic administration, a therapeutically effective dose can be estimated initially from in vitro assays. For example, a dose can be formulated in animal models to achieve a circulating concentration range that includes the $IC_{50}$ as determined in cell culture. Such information can be used to more accurately determine useful doses in humans. Initial dosages can also be estimated from in vivo data, e.g., animal models, using techniques that are well known in the art. One having ordinary skill in the art could readily optimize administration to humans based on animal data.

Dosage amount and interval may be adjusted individually to provide plasma levels of the compounds that are sufficient to maintain therapeutic effect. One having skill in the art will be able to optimize therapeutically effective local dosages without undue experimentation.

The amount of compound administered will, of course, be dependent on the subject being treated, on the subject's weight, the severity of the affliction, the manner of administration, and the judgment of the prescribing physician. The therapy may be repeated intermittently while symptoms are detectable or even when they are not detectable. The therapy may be provided alone or in combination with other drugs.

Methods of Administration

The invention provides methods of treatment comprising administering to a subject an effective amount of an agent of the invention. In a preferred aspect, the agent is substantially purified (e.g., substantially free from substances that limit its effect or produce undesired side-effects). The subject is preferably an animal, e.g., such as cows, pigs, horses, chickens, cats, dogs, etc., and is preferably a mammal, and most preferably human.

Various delivery systems are known and can be used to administer an agent of the invention, e.g., encapsulation in liposomes, microparticles, microcapsules, recombinant cells capable of expressing the compound, receptor-mediated endocytosis (see, e.g., Wu and Wu, 1987, J. Biol. Chem. 262:4429-4432), construction of a nucleic acid as part of a retroviral or other vector, etc. Methods of introduction can be enteral or parenteral and include but are not limited to intradermal, intramuscular, intraperitoneal, intravenous, subcutaneous, intranasal, and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. Administration can be acute or chronic (e.g. daily, weekly, monthly, etc.) or in combination with other agents.

In another embodiment, the active agent can be delivered in a vesicle, in particular a liposome (see Langer (1990) Science 249:1527-1533). In yet another embodiment, the active agent can be delivered in a controlled release system. In one embodiment, a pump may be used (see Langer (1990) supra). In another embodiment, polymeric materials can be used (see Howard et al. (1989) J. Neurosurg. 71:105). In another embodiment where the active agent of the invention is a nucleic acid encoding a protein, the nucleic acid can be administered in vivo to promote expression of its encoded protein, by constructing it as part of an appropriate nucleic acid expression vector and administering it so that it becomes intracellular, e.g., by use of a retroviral vector (see, for example, U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., 1991, Proc. Natl. Acad. Sci. USA 88:1864-1868), etc. Alternatively, a nucleic acid can be introduced intracellularly and incorporated within host cell DNA for expression, by homologous recombination.

Specific Embodiments

The experiments described below examined the effect of a receptor-based VEGF antagonist ("VEGF trap", SEQ ID NO:2, Regeneron Pharmaceuticals) on animals bearing U-87 MG human glioma tumors. The VEGF trap was efficacious in producing a significant increase in survival compared to hFc or PBS-treated animals (p<0.007, log-rank test). These results show that the VEGF trap induced a potent antiglioma effect with significant impact on initial disease and disease burden that results in significant prolongation of survival.

As described more fully below, the evolution of growth patterns and angiogenesis in the intracranial U-87 MG human glioma xenograft was monitored. Serial temporal examination of the brains showed that tumors grew to a volume of 0.3 $mm^3$ and exhibited a very low micarovascular density (MVD=6 vessels/0.5 $mm^2$) with central necrosis within four days of implantation, and peripheral reactive vasculature. After day four, necrosis was not observed. At day 10 after implantation, tumors were sphere-like masses of cells (30-45 $mm^3$) with development of robust tumor vsculature (MVD=30-35 vessels/0.5 $mm^2$). According to the described tumoral angiogenesis, VEGF trap (SEQ ID NO:2) (25 mg/kg/sc, twice a week for a total of 3 weeks) was administered to animals bearing U-87 MG intracranial xenografts at different time points (0, 4 and 10 days after cell implantation). VEGF trap treatment of initial disease, as well as disease burden, was efficacious in producing a significant increase in survival, compared to hFc or PBS-treated animals (p<0.007, log-rank test). High serum VEGF trap levels (approximately greater than 50 µg/ml) were detected in the serum in all these animals after the initial dose, suggesting an efficient systemic biodistribution.

Other features of the invention will become apparent in the course of the following descriptions of exemplary embodiments which are given for illustration of the invention and are not intended to be limiting thereof.

EXAMPLES

The following example is put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1

Effect of VEGF Antagonist in the U-87 MG Intracranial Gloma Model

Nude mice (female, 4 weeks old) were injected intracranially with 5×10$^5$ U-87 MG cells (Lal et al., (2000) J Neurosurgery 92:326-33; Lee et al. (2006) Neoplasia in press) and 0, 4, or 10 days later, VEGF trap, hFc or vehicle (PBS) was administered subcutaneous twice weekly for 3 weeks. Animals showing generalized or localized symptoms of toxicity were sacrificed. All animal studies were performed at the veterinary facilities at M.D. Anderson Cancer Center in accordance with institutional guidelines. Results are shown in Table 1 (NA=non applicable. Overall survival in VEGF trap, hFc, and PBS-treated animals were plotted as Kaplan-Meier curves and analyzed using log-rank test. The mean and corresponding 95% confidence (CI) levels are shown in Table 1. Thus, VEGF trap treatment prolonged the survival of U-87 MG-bearing animals (compared to the survival of control-treated (hFc) U-87 MG-bearing animals) from 29 days to 37 days (when treatment was initiated day 0 after cell implantation); from 29 days to 35.5 days (when treatment was initiated on day 4 after cell implantation); and from 30 days to 44 days (when treatment was initiated on day 10 after cell implantation). Those differences were statistically significant in the three experiments described above (P<0.007, log-rank test). These data suggest that VEGF treatment of initial disease (equivalent to the starting day treatment 0 or 4 after cell implantation), as well as disease with tumor burden (equivalent to the starting treatment day 10 after cell implantation) was efficacious in producing a significant increase in survival compared to hFc- and PBS-treated animals.

VEGF trap levels in serum where determined by ELISA in animals treated following the three schedule treatments described above (subcutaneous injections of VEGF trap starting 0, 4, or 10 days after U-87 MG intracranial implantation). The results, shown in Table 2, show that high serum levels of VEGF trap were detected in animals three days after the initial dose, suggesting an efficient systemic distribution. Included in Table 2 are the technical background levels detected in PBS- or hFc-treated animals.

TABLE 1

| | Mean Survival Time with Treatment | | | |
|---|---|---|---|---|
| Schedule | Treatment | N | Mean (days) | 95% CI (days) |
| A (Day 0) | VEGF Trap | 10 | 37 | 35, NA |
| | hFc | 10 | 29 | 25, NA |
| | PBS | 9 | 29 | 25, NA |
| B (Day 4) | VEGF Trap | 10 | 35.5 | 29, NA |
| | hFc | 10 | 29 | 29, NA |
| | PBS | 8 | 26.5 | 25, NA |
| C (Day 10) | VEGF Trap | 15 | 44 | 43, 45 |
| | hFc | 10 | 30 | 27, NA |
| | PBS | 10 | 30 | 28, NA |

TABLE 2

| | Serum Levels of VEGF Trap | |
|---|---|---|
| Schedule | Treatment | Serum Levels VEGF Trap (µg/ml) |
| A (Day 0) | VEGF Trap | 84.98 ± 15.38 |
| | hFc | 0.07 ± 0.11 |
| | PBS | 0.13 ± 0.23 |
| B (Day 4) | VEGF Trap | 66.52 ± 27.03 |
| | hFc | 0.1 ± 0.13 |
| | PBS | 0.16 ± 0.25 |
| C (Day 10) | VEGF Trap | 57.24 ± 14.17 |
| | hFc | 0.03 ± 0.07 |
| | PBS | 0.01 ± 0.03 |

The present invention may be embodied in other specific forms without departing from the spirit or essential attributes thereof.

We claim:

1. A method of treating a human patient suffering from a brain tumor, comprising administering a therapeutically effective amount of a vascular endothelial growth factor (VEGF) antagonist to the human patient, wherein the VEGF antagonist is a dimeric protein comprising two fusion polypeptides, wherein each fusion polypeptide consists of VEGFR1R2-FcΔC1(a) (SEQ ID NO:2).

2. The method of claim 1, wherein administration is intraparenchymal, intracavitary, convection-enhanced delivery to the brain or to the tumor bed, or systemically via subcutaneous, intramuscular, intradermal, intraperitoneal, or intravenous administration.

3. The method of claim 2, wherein administration is by subcutaneous injection.

4. The method of claim 2, wherein administration is by intravenous injection.

5. The method of claim 1, wherein the brain tumor is a primary brain tumor.

6. The method of claim 1, wherein the patient is further treated with a chemotherapeutic agent.

7. The method of claim 1, wherein the amount of VEGF antagonist administered is in a dosage range between about 0.3 mg/kg to about 30 mg/kg.

8. The method of claim 7, wherein the dosage range is between 0.5 to 10 mg/kg.

9. The method of claim 8, wherein the dosage range is between 1 to 6 mg/kg.

10. The method of claim 1, wherein the VEGF antagonist is administered once a month.

11. The method of claim 10, wherein the VEGF antagonist is administered at least once a week.

12. A method of treating a human patient suffering from glioblastoma, comprising administering an effective amount of a vascular endothelial growth factor (VEGF) antagonist to the human patient, wherein the VEGF antagonist to the human patient, wherein the VEGF antagonist is a dimeric protein comprising two fusion polypeptides, wherein each fusion polypeptide consists of VEGFR1R2-FcΔC1(a) (SEQ ID NO:2).

* * * * *